US006436874B1

(12) United States Patent
Kuah et al.

(10) Patent No.: US 6,436,874 B1
(45) Date of Patent: Aug. 20, 2002

(54) SYNERGISTIC HERBICIDAL AGENTS BASED ON LEAF HERBICIDES CONTAINING PHOSPHORUS, IMIDAZOLINONES AND HORMONE WEED KILLERS

(75) Inventors: Tai Choon Kuah; Soon Huat Ooi; Gill Jagdish Singh; Daniel Anthonysamy, all of Kuala Lumpur (MY)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/647,830

(22) PCT Filed: Mar. 30, 1999

(86) PCT No.: PCT/EP99/02187

§ 371 (c)(1),
(2), (4) Date: May 11, 2001

(87) PCT Pub. No.: WO99/52367

PCT Pub. Date: Oct. 21, 1999

(30) Foreign Application Priority Data

Apr. 8, 1998 (DE) .......................................... 198 15 820

(51) Int. Cl.[7] .......................... A01N 43/50; A01N 57/02
(52) U.S. Cl. ...................................................... 504/128
(58) Field of Search .......................................... 504/128

(56) References Cited

U.S. PATENT DOCUMENTS

| | | | | |
|---|---|---|---|---|
| 4,382,812 A | * | 5/1983 | Takematsu et al. ............. | 71/86 |
| 4,552,584 A | * | 11/1985 | Takematsu et al. ............. | 71/86 |
| 5,461,019 A | | 10/1995 | Willms et al. ............... | 504/130 |
| 5,525,578 A | | 6/1996 | Langelüddeke et al. .... | 504/128 |

FOREIGN PATENT DOCUMENTS

| | | |
|---|---|---|
| CA | 1291344 | 10/1991 |
| DE | 2856260 A1 | 7/1979 |
| DE | 4019362 A1 | 1/1991 |
| EP | 0 252 237 A2 | 1/1988 |
| EP | 0 502 014 | 9/1992 |
| EP | 0 569 944 A2 | 11/1993 |
| GB | 2 011 416 | 10/1982 |
| GB | 2 233 229 | 5/1992 |

OTHER PUBLICATIONS

Flint et al., "Effects of Glyphosate Combinations with 2,4–D or Dicamba On Field Bindweed (Convolvulus Arvensis)", Weed Science, 1989, vol. 37, pp. 12–18.

Willard et al., "Influence of Herbicide Combinations and Application Technology on Cogongrass (*Imperata cylindrica*) Control", Weed Technology, 1997, vol. 11, pp. 76–80.

Lanie et al., "Herbicide Combinations for Soybean (*Glycine max*) Planted in Stale Seedbed", Weed Technology, 1994, vol. 8, pp. 17–22.

Bruff et al., "Tank–mix Combinations for Weed Control in Stale Seedbed Soybean (*Glycine max*)", Weed Technology, 1992, vol. 6, pp. 45–51.

* cited by examiner

*Primary Examiner*—S. Mark Clardy
(74) *Attorney, Agent, or Firm*—Frommer Lawrence & Haug LLP

(57) ABSTRACT

Herbicidal compositions containing a combination (A)+(B)+(C) of (A) leaf-acting herbicides from the group glufosinate and its esters and salts, glufosinate-peptides, such as bialaphos, and its salts, glyphosate and its salts, for example also sulfosate, (B) imidazolinone herbicides and their salts and (C) one or more active compounds from the group of the growth-promoting herbicides and their esters and salts have synergistic herbicidal action.

8 Claims, No Drawings

SYNERGISTIC HERBICIDAL AGENTS BASED ON LEAF HERBICIDES CONTAINING PHOSPHORUS, IMIDAZOLINONES AND HORMONE WEED KILLERS

The invention is in the field of the crop protection compositions which can be used against undesirable vegetation and which contain a combination of more than two herbicides as herbicidally active compounds.

More specifically, the invention relates to herbicidal compositions which comprise, as active compound, a broad-spectrum herbicide of the type of the leaf-acting herbicides, such as glufosinate, bialaphos, glyphosate and sulfosate in combination with two other herbicides from certain other substance classes.

The abovementioned leaf-acting herbicides are taken up via the green parts of the plants and are known as broad-spectrum herbicides or total herbicides; see "The Pesticide Manual" 11th Edition, British Crop Protection Council 1997, pp. 120, 382 and 646. They are predominantly employed by the post-emergence method, for controlling broad-leaved weeds and weed grasses in plantation crops and on uncultivated land and, by means of specific application techniques, also for inter-row treatment in agricultural row crops such as maize, cotton and the like. A further area of use of increasing importance is in transgenic crops of plants which are resistant to the herbicides.

The efficacy of herbicides depends, inter alia, on the type of herbicide employed, on its application rate, on the formulation, on the harmful plants to be controlled in each case, on the climatic and soil conditions, etc. A further criterium is the duration of the action, or the rate of degradation of the herbicide. Also to be taken into account are, if appropriate, changes in the susceptibility of harmful plants toward an active compound which may occur on prolonged use or when geographically restricted; loss of activity up to resistance of harmful plants can only be compensated to a certain degree by higher application rates of the herbicides.

Owing to the large number of possible influencing factors, there is virtually no individual active compound in which the desired properties for various requirements, in particular with regard to the species of the harmful plants and the climatic zones, are combined. There is additionally the permanent object of achieving the effect with ever lower herbicide application rates. A lower application rate does not only reduce the amount of an active compound which is required for the application, but usually also reduces the amount of formulation auxiliaries required. Both reduce the economic expense and improve the ecological compatibility of the herbicide treatment.

A method which is frequently employed for improving the property profile of a herbicide consists of the combination of the active compound with one or more other active compounds which contribute the desired additional properties. However, when two or more active compounds are applied in combination, it is not uncommon for phenomena of physical and biological incompatibility to occur, for example lack of stability of a coformulation, decomposition of an active compound or antagonism of the active compounds. In contrast, what is desired are combinations of active compounds having a favorable activity profile, high stability and as synergistically enhanced an activity as possible which permits a reduction of the application rate, compared with the individual application of the active compounds to be combined.

Surprisingly, it has now been found that active compounds from the group of the abovementioned leaf-acting herbicides interact in a particularly favorable manner with a combination of herbicides from the group of the imidazolinones and the growth-promoting herbicides.

The invention accordingly provides herbicidal compositions comprising an effective amount of a combination of A) one or more leaf-acting herbicides from the group of the compounds of the formulae (A1) and (A2) and their esters and salts,

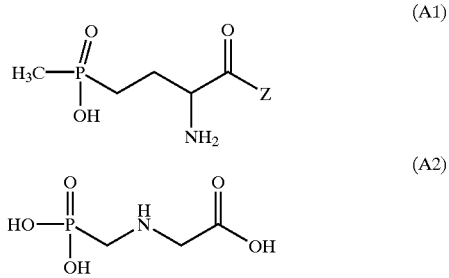

in which Z is a radical of the formula —OH or a peptide radical of the formula —NHCH(CH$_3$)CONHCH(CH$_3$)COOH or —NHCH(CH$_3$)CONHCH[CH$_2$CH(CH$_3$)$_2$]COOH, B) one or more active compounds from the group of the imidazolinone herbicides, preferably imazapyr, imazethapyr, imazamethabenz, in particular imazapyr, and their salts, C) one or more active compounds from the group of the growth-promoting herbicides, preferably 2,4-D and MCPA.

It is already known from EP-A-0252237 (CA-A-1291344) to combine glufosinate and its salts with imidazolinone herbicides, in which synergistic activity increases have been observed. From EP-A-0502014 (U.S. Pat. No. 5,525,578), it is known that the activity of combinations of glufosinate and imidazolinones can be increased by addition of certain surfactants, for example from the series of the fatty alcohol polyglycol ether sulfates.

Synergistic combinations of glufosinate with growth-promoting herbicides such as 2,4-D, MCPA, 2,3,6-TBA, CMPP, dichlorprop, 2,4-DB, MCPB and dicamba are known from DE-A-2856260 (GB-A-2011416).

Int. Patent Appl. No. PCT/EP99/03987 (Aventis CS Ref.: AGR1998/M216) SUPPLEMENTARY SHEET 3a From DE-A-4019362, it is known to combine glyphosate or its derivatives with certain surfactants as activators, it being possible for the combination to comprise further known active compounds. Possible active combination partners which are mentioned are, inter alia, 2,4-D, 2,4-DB, MCPP or else imidazolinones, such as imazaquin and imazapur.

From EP-A-0569944, it is known to combine herbicidal imidazolinones from the group consisting of imazaquin, imazethapyr and imazamethapyr with herbicides from the group consisting of dicamba, 2,4-D, bromoxynil, pyridate, cyclohexanediones and sulfonylureas, where synergistic activity increases were observed, too.

Furthermore, reports on field trials of the following combinations are known: glyphosate and 2,4-D or dicamba (see Weed Science, Vol. 37, No.1, 1989, pp.12–18), glyphosate and imazaquin (see Weed Technology, Vol. 6, No. 1, 1992, pp. 45–51), glufosinate or glyphosate and imazaquin (see Weed Technology, Vol. 8, No. 1, 1994, pp. 17–22) and glyphosate and imazapyr (see Weed Technology, Vol.11, No. 1, 1997, pp. 76–80).

A mixture of imazamethabenz and mecoprop was commercially available or recommended (see "The Pesticide Manual" 10th edition 1994, p. 583, section "Applications").

Surprisingly, the combinations of herbicides A+B+C according to the invention permit synergistic activity increases which exceed, by a wide margin and in an unexpected manner, the activity increases achieved with the two-compound combinations A+B and A+C.

The formula (A1) embraces all stereoisomers and mixtures thereof, in particular the racemate and the respective enantiomer which is biologically active, for example L-glufosinate and its salts. Examples of active compounds of the formula (A1) are the following:
(A1.1) Glufosinate in the narrow sense, i.e. D,L-2-amino-4-[hydroxy(methyl)phosphinyl]butanoic acid,
(A1.2) Glufosinate-monoammonium salt,
(A1.3) L-Glufosinate, L- or (2S)-2-amino-4-[hydroxy (methyl)phosphinyl]-butanoic acid,
(A1.4) L-Glufosinate-monoammonium salt, (A1.5) Bialaphos (or bilanafos), i.e. L-2-amino-4-[hydroxy(methyl) phosphinyl ]-butanoyl-L-alanyl-L-alanine, in particular its sodium salt.

Glufosinate is usually employed in the form of a salt, preferably the ammonium salt. The racemate of glufosinate or glufosinate-ammonium on its own is usually applied in dosages between 200 and 1000 g of AS/ha (=g of a.i./ha= gram of active substance per hectare). At these dosages, glufosinate is effective especially when it is taken up via green parts of the plant. Since it is degraded microbially in the soil within a few days, it is does not persist in the soil. This applies similarly also to the related active compound bialaphos-sodium; see "The Pesticide Manual" 11th edition, British Crop Protection Council 1997, p. 382 and p. 120.

In the combinations according to the invention, there is generally considerably less active compound (A1) required, for example an application rate in the range from 20 to 500, preferably from 20 to 100, gram of active substance glufosinate per hectare (g of AS/ha or g of a.i./ha). The corresponding amounts, preferably amounts converted into mole per hectare, are also valid for glufosinate-ammonium and bialafos or bialafos-sodium.

Examples of compounds (A2) are
(A2.1) Glyphosate, i.e. N-(phosphonomethyl)glycine,
(A2.2) Glyphosate-monoisopropylammonium salt,
(A2.3) Glyphosate-sodium salt,
(A2.4) Glyphosate-monoammonium salt,
(A2.5) Sulfosate, i.e. N-(phosphonomethyl)glycine-trimesium salt=N-(phosphonomethyl)glycine-trimethylsulfonium salt,
(A2.6) Glyphosate-monoethyl ester.

Glyphosate is usually employed in the form of a salt, preferably the monoisopropylammonium salt or the trimethylsulfoxonium (trimesium) salt (sulfosate). Based on the free acid glyphosate, the individual dosage is in the range from 1 to 5 kg of AS/ha. In many aspects and areas of use, glyphosate is similar to glufosinate. In the combinations according to the invention, application rates in the range from 20 to 500, preferably from 20 to 100, g of AS/ha of glyphosate are generally required.

Examples of compounds (B) are
(B1) Imazapyr and its salts and esters,
(B2) Imazethapyr and its salts and esters,
(B3) Imazamethabenz and its salts and esters,
(B4) Imazamethabenz-methyl,
(B5) Imazamox and its salts and esters,
(B6) Imazaquin and its salts and esters, for example the ammonium salt,
(B7) AC 263,222 (imazapic) and its salts and esters.

The application rates of the individual herbicides are generally in the range from 0.25 to 2 kg of AS/ha. In the combinations according to the invention, application rates in the range from 20 to 500, preferably from 20 to 100, g of AS/ha of the imidazolinones, preferably of imazapyr, are generally required.

Examples of compounds (C) are growth-promoting herbicides such as
(C1) 2,4-D[=(2,4-dichlorophenoxy)acetic acid] and its salts and esters,
(C2) MCPA[=(4-chloro-2-methylphenoxy)acetic acid] and its salts and esters,
(C3) 2,3,6-TBA[=2,3,6-trichlorobenzoic acid] and its salts and esters,
(C4) CMPP (Mecoprop) (C4.1)[=(RS)-2-(4-chloro-2-methylphenoxy)propionic acid], Mecoprop-P (C4.2)[=(+)-(R)-2-(4-chloro-2-methylphenoxy)propionic acid] and its salts and esters,
(C5) Dichlorprop (C5.1)[=(RS)-2-(2,4-dichlorophenoxy) propionic acid], Dichlorprop-P (C5.2)[=(+)-(R)-2-(2,4-dichlorophenoxy)propionic acid] and its salts and esters,
(C6) 2,4-DB[=4-(2,4-dichlorophenoxy)butanoic acid] and its salts and esters,
(C7) MCPB[=4-(4-chloro-2-methylphenoxy)butanoic acid] and its salts and esters,
(C8) Dicamba[=3,6-dichloro-2-methoxybenzoic acid] and its salts and esters.

The abovementioned active compounds are likewise all known; see "The Pesticide Manual" 11th edition, British Crop Protection Council 1997. In the combinations according to the invention, application rates in the range from 10 to 1000, preferably from 10 to 80, g of AS/ha of the growth-promoting herbicides, preferably of 2,4-D and MCPA, in particular of 2,4-D, are generally required.

The ratios by weight of the components A:B:C can be varied within wide ranges. The ratio is preferably in the range from 1:0.5:0.1 to 1:2:2, in particular in the range from 1:0.6:0.2 to 1:1:1; the abovementioned ratios preferably apply for combinations with herbicides of the formula (A1). Optimum ratios may depend on the respective area of application, weed spectrum and on the active compound combination employed and can be determined in preliminary experiments.

The compositions according to the invention can be employed for the selective control of annual and perennial harmful plants in plantation crops such as oil palm, coconut palm, India-rubber tree, citrus, pineapples, cotton, coffee, cocoa and the like, and also in fruit production and viticulture. Equally, the combinations according to the invention can be employed in arable crop production using the no-till, or zero-till, method. A further area of use is the control of harmful plants in transgenic crops or crops selected in a classical way which are resistant to the active compounds (A)+(B)+(C).

However, it is also possible to employ the compositions according to the invention in a non-selective manner on paths, open spaces, industrial sites, etc., to keep these areas free from undesirable vegetation.

The compositions according to the invention act against a broad spectrum of weeds.

They are suitable, for example, for controlling annual and perennial weeds such as, for example, from the species Agropyron, Paspalum, Cynodon, Imperata, Pennisetum, Convolvulus, Cirsium, Rumex, Hedyotis, Asystasia, Borraria, Clidemia, Ageratum, Ottochloa, Axonopus, Brachiara, Digitaria, Panicum, Echinochloa, and the like. They can preferably be used against tropical weeds in plantation crops, for example against Hedyotis verticillata, Asystasia intrusa, Borraria tatifolia, Clidemia hirta, Ageratum conyzoides, Ottochloa nodosa, Axonopus compressus, Brachiara mutica, Digitaria horizontalis, Panicum maximum, Echinochloa colona.

The herbicidal compositions according to the invention have a long-term herbicidal action with a rapid onset. Rainfastness of the active compounds in the combinations according to the invention is good. A particular advantage is the fact that the effective dosages of compounds (A), (B) and (C) used in the combinations are so low that their soil action is reduced considerably. This makes their use in sensitive crops possible for the first time, and, additionally, contamination of the groundwater is virtually avoided. The combinations according to the invention of active compounds allow the required application rates of the active compounds to be reduced considerably.

The invention accordingly also provides a method for controlling undesirable vegetation which comprises applying one or more herbicides of type (A) with one or more herbicides of type (B) and one or more herbicides of type (C) to the harmful plants, parts of these plants or the area under cultivation.

When herbicides of type (A)+(B)+(C) are applied jointly, superadditive (=synergistic) effects are observed. The activity in the combinations is more pronounced than the expected sum of the activities of the individual herbicides employed or the sum of the activities of combinations of two herbicides, such as, for example, ½(A)+(B) and ½(A)+(C), or a combination of two herbicides (A)+(B), (A)+(C) or (B)+(C) and the activity of the respective individual herbicide (A), (C), (B) or (C). The synergistic effects permit the application rate to be reduced, a broader spectrum of broad-leaved weeds and weed grasses to be controlled, more rapid onset of the herbicidal action, a more prolonged action, better control of the harmful plants by only one application, or few applications, and widening of the period of time within which the product can be used. These properties are required in weed control practice to keep agricultural crops free from undesirable competing plants and thus to ensure and/or to increase quality and quantity of the yields. These novel combinations markedly surpass the prior art in view of the thus-described properties.

The active compound combinations according to the invention can either exist in the form of mixed formulations of the three components, if appropriate together with other customary formulation auxiliaries, which mixed formulations are then applied in the usual manner in the form of a dilution with water, or else they can be prepared in the form of so-called tank mixes by joint dilution with water of the components which are formulated separately, or partly separately.

The compounds (A), (B) and (C) or their combinations can be formulated in various ways, depending on the prevailing biological and/or chemical-physical parameters. Suitable general possibilities for formulations are, for example: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed dressing products, granules for soil application or for spreading or water-dispersible granules (WG), ULV formulations, microcapsules or waxes.

The individual types of formulation are known in principle and are described, for example, in: Winnacker-Küchler, "Chemische Technologie" [Chemical Technology], Vol. 7, C. Hauser Verlag Munich, 4th edition 1986; van Valkenburg, "Pesticides Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Volume 7, C. Hauser Verlag Munich, 4th ed. 1986.

Based on these formulations, it is also possible to prepare combinations with other pesticidally active substances, such as other herbicides, fungicides or insecticides, and also safeners, fertilizers and/or growth regulators, for example in the form of a ready mix or tank mix.

Wettable powders are preparations which are uniformly dispersible in water and which, besides the active compound, also comprise ionic or nonionic surfactants (wetting agents, dispersants), for example polyethoxylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutyinaphthalenesulfonate or else sodium oleoylmethyltaurinate, in addition to a diluent or an inert substance.

Emulsifiable concentrates are prepared by dissolving the active compound in an organic solvent, for example butanol, cyclohexanone, dimethylformamide, xylene or else higher-boiling aromatics or hydrocarbons, with the addition of one or more ionic or nonionic surfactants (emulsifiers). Examples of emulsifiers which can be used are: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty esters or polyoxyethylene sorbitol esters.

Dusts are obtained by grinding the active compound with finely divided solid materials, for example talc, natural clays, such as kaolin, bentonite and pyrophyllite, or diatomaceous earth.

Granules can be prepared either by spraying the active compound onto absorptive, granulated inert material, or by applying active compound concentrates to the surface of carriers, such as sand, kaolinite or granulated inert material, with the aid of binders, for example polyvinyl alcohol, sodium polyacrylate or else mineral oils. Suitable active compounds can also be granulated in the manner customary for the preparation of fertilizer granules, if desired as a mixture with fertilizers. Water-dispersible granules are, in general, prepared by processes such as spray-drying, fluidized-bed granulation, disk granulation, mixing using high-speed mixers, and extrusion without solid inert material.

The agrochemical preparations generally comprise from 0.1 to 99 percent by weight, in particular from 2 to 95% by weight, of active compounds of types A and/or B, the following concentrations being customary, depending on the type of formulation: In wettable powders, the active compound concentration is, for example, approximately 10 to 95% by weight, the remainder to 100% by weight being composed of customary formulation components. In the case of emulsifiable concentrates, the active compound concentration can be, for example, from 5 to 80% by weight.

Formulations in the form of dusts in most cases comprise from 5 to 20% by weight of active compound, sprayable solutions approximately 0.2 to 25% by weight of active compound.

In the case of granules, such as dispersible granules, the active compound content depends partly on whether the active compound is in liquid or solid form and on which granulation auxiliaries and fillers are used. In general, the content in the water-dispersible granules amounts to between 10 and 90% by weight.

In addition, the active compound formulations mentioned comprise, if appropriate, the tackifiers, wetting agents, dispersants, emulsifiers, preservatives, antifreeze agents, solvents, fillers, colorants, carriers, antifoams, evaporation inhibitors and pH or viscosity regulators which are customary in each case.

It is known, for example, that the activity of glufosinate-ammonium and that of its L-enantiomer can be improved by surfactants, preferably by wetting agents from the series of the alkyl polyglycol ether sulfates containing, for example, 10 to 18 carbon atoms and being used in the form of their alkali metal or ammonium salts, or else as magnesium salt, such as sodium $C_{12}/C_{14}$-fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227–232 (1988). Furthermore, it is known that alkyl polyglycol ether sulfates are also suitable for use as penetration-promoting auxiliaries and activity enhancers for a number of other herbicides, including, inter alia, herbicides from the series of the imidazolinones; see EP-A-0502014.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions, are conventionally not diluted any further with other inert substances prior to use.

The active compounds can be applied to the plants, parts of the plants, seeds of the plants or the area under cultivation (tilled soil), preferably to the green plants and parts of the plants and, if desired, additionally to the tilled soil.

A possible use is the joint compound of the active compounds in the form of tank mixes, where the concentrated formulations of the individual active substances, in the form of their optimal formulations, are mixed jointly with water in the tank, and the spray mixture obtained is applied.

A joint herbicidal formulation of the combination according to the invention of the active compounds (A) and (B) and (C) has the advantage that it can be applied more easily because the amounts of the components have already been adjusted to one another to the correct ratio. Moreover, the auxiliaries of the formulation can be selected to suit each other in the best possible way, while a tank mix of various formulations may result in undesirable combinations of auxiliaries.

A. General Formulation Examples
a) A dust is obtained by mixing 10 parts by weight of an active compound/active compound mixture and 90 parts by weight of talc as inert substance and comminuting the mixture in a hammer mill.
b) A wettable powder which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.
c) A dispersion concentrate which is readily dispersible in water is obtained by mixing 20 parts by weight of an active compound/active compound mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.
d) An emulsifiable concentrate is obtained from 15 parts by weight of an active compound/active compound mixture, 75 parts by weight of cyclohexanone as solvent and 10 parts by weight of ethoxylated nonylphenol as emulsifier.
e) Water-dispersible granules are obtained by mixing
   75 parts by weight of an active compound/active compound mixture,
   10 parts by weight of calcium lignosulfonate,
   5 parts by weight of sodium lauryl sulfate,
   3 parts by weight of polyvinyl alcohol and
   7 parts by weight of kaolin
grinding the mixture in a pinned-disk mill and granulating the powder in a fluidized bed by spraying on water as granulation liquid.
f) Water-dispersible granules are also obtained by homogenizing and precomminuting, in a colloid mill,
   25 parts by weight of an active compound/active compound mixture,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
subsequently grinding the mixture in a bead mill and atomizing and drying the resulting suspension in a spray tower by means of a single-substance nozzle.

BIOLOGICAL EXAMPLES

Example 1

Field Trial

In an oil palm plantation, the economically important tropical weed Hedyotis verticillata was grown on plots of the dimensions 2×5 m under natural outdoor conditions and treated with the herbicides A1.2, B1 and C1 or their mixtures in a tank mix under standard conditions using a plot sprayer, at a water application rate of 450 liters of water per hectare (over-the-top application to the weeds; plant density initially more than 95% ground coverage). At intervals of 1, 2, 3, 4, 5, 6, 7 and 8 weeks after the application, the herbicidal efficacy of the active compounds or active compound mixtures was evaluated visually on the basis of the treated plots, in comparison with untreated control plots. The damage to and development of all above-ground parts of the plants were recorded. Evaluation was carried out using a percentage scale (100% effect=all plants killed; 50% effect=50% of the plants and the green parts of the plants killed; 0% effect=no noticeable effect=like control plot). The evaluation values of in each case 4 plots were averaged. The results are summarized in Table 1.

The comparison shows that the three-component mixtures (trials 1 and 2) have a herbicidal activity that is in most cases higher, in some cases considerably higher, than the sum of the activities of the individual herbicides or the sum of the activities of corresponding two-component mixtures or of two-component mixtures and individual herbicides; compare, for example, trial No. 1 with trials No. 6+15, No. 7+14 or No. 5+10 or trial No. 2 with trials No. 8+14, No. 3+9 or No. 4+16, in each case in the same week after application.

If the observed activity values already exceed the formal sum of the values for the trials with two-component or individual applications, they also exceed the expected value according to Colby which is calculated using the following formula (cf. S. R. Colby; in Weeds 15 (1967) pp. 20 to 22):

$$E=A+B+C-(A \cdot B \cdot C/1000) \text{ or } E=AB+C-(AB \cdot C/100) \text{ or } E=AB+AC-(AB \cdot AC/100)$$

The figures denote: A, B, C, AB, AC=activity of the active compounds A, B, C, A+B and A+C, respectively, in % at a, b, c, a+b and a+c, respectively, g of AS/ha; E=expected value in % at a+b+c, g of AS/ha.

According to all criteria, the observed values of the trials 1 and 2 exceed the expected values according to Colby.

their mixtures in a tank mix were applied under standard conditions (over-the-top application using a plot sprayer, water application rate 450 l/ha). In intervals of 4, 7, 13, 17 and 21 weeks after the application, the herbicidal efficacy of the active compounds or their mixtures was evaluated visually on the basis of the treated plots, in comparison with untreated control plots. The damage to and the development of all above-ground parts of the plants were recorded. Evaluation was carried out as described in Example 1. The results are summarized in Table 2.

The comparison of the evaluation values shows that the three-component mixture (trial 1) has a considerably better long-term activity than the sum of the herbicidal activities of the individual herbicides (see the experiments after 13 to 21 weeks after application).

TABLE 2

Herbicidal activity against *Asystasia intrusa* in rubber tree plantation

| No. | Active compound(s) | Dose (g of AS/ha) | Activity (%), w. after appl. | | | | |
|---|---|---|---|---|---|---|---|
| | | | 4 | 7 | 13 | 17 | 21 |
| 1 | A1.2 + B1 + C1 | 60 + 50 + 40 | 90 | 90 | 80 | 80 | 80 |
| 2 | A1.2 | 60 | 23 | 5 | 0 | 0 | 0 |
| 3 | B1 | 50 | 45 | 40 | 40 | 47 | 53 |
| 16 | C1 | 40 | 77 | 67 | 20 | 10 | 8 |

Abbreviations for Table 2: See abbreviations for Table 1

TABLE 1

Herbicidal activity against *Hedyotis verticillata* in oil palm plantations

| No. | Active compound(s) | Dose (g of AS/ha) | Herbicidal activity (%), w. after appl. | | | | | | | |
|---|---|---|---|---|---|---|---|---|---|---|
| | | | 1 | 2 | 3 | 4 | 5 | 6 | 7 | 8 |
| 1 | A1.2 + B1 + C1 | 50 + 50 + 40 | 68 | 73 | 90 | 100 | 100 | 100 | 99 | 95 |
| 2 | A1.2 + B1 + C1 | 80 + 50 + 20 | 75 | 80 | 100 | 100 | 100 | 100 | 100 | 100 |
| 3 | A1.2 + B1 | 40 + 50 | 45 | 38 | 40 | 25 | 18 | 10 | 10 | 0 |
| 4 | A1.2 + B1 | 80 + 50 | 60 | 50 | 48 | 40 | 40 | 38 | 33 | 8 |
| 5 | A1.2 + B1 | 25 + 50 | 40 | 38 | 33 | 35 | 13 | 10 | 10 | 0 |
| 6 | A1.2 + C1 | 50 + 50 | 45 | 38 | 35 | 20 | 15 | 10 | 10 | 0 |
| 7 | A1.2 + C1 | 50 + 40 | 50 | 40 | 33 | 20 | 10 | 10 | 10 | 0 |
| 8 | A1.2 + C1 | 80 + 20 | 60 | 58 | 50 | 45 | 40 | 30 | 23 | 10 |
| 9 | A1.2 + C1 | 40 + 20 | 50 | 38 | 30 | 20 | 10 | 10 | 10 | 0 |
| 10 | A1.2 + C1 | 25 + 40 | 40 | 34 | 30 | 20 | 10 | 12 | 10 | 7 |
| 11 | A1.2 | 25 | 35 | 28 | 23 | 20 | 10 | 10 | 10 | 0 |
| 12 | A1.2 | 50 | 35 | 25 | 20 | 20 | 10 | 10 | 10 | 0 |
| 13 | A1.2 | 80 | 58 | 45 | 40 | 40 | 40 | 30 | 28 | 8 |
| 14 | B1 | 50 | 8 | 5 | 5 | 5 | 10 | 13 | 15 | 15 |
| 15 | C1 | 40 | 6 | 5 | 5 | 4 | 0 | 0 | 0 | 0 |
| 16 | C1 | 20 | 6 | 5 | 5 | 1 | 0 | 0 | 0 | 0 |

Abbreviations in Table 1 (see below):
w. after appl. = week(s) after application
A1.2 = Glufosinate-ammonium (g of AS/ha is based on the amount of salt)
B1 = Imazapyr (g of AS/ha is based on the amount of acid equivalent)
C1 = 2,4-D-sodium salt (g of AS/ha is based on the amount of salt)

Example 2

Field Trial

In a rubber tree plantation, plots with the tropical weed Asystasia intrusa were grown under natural outdoor conditions (dimensions of the plots 2 x 5 m). The herbicides or Example 3

Field Trial

In a rubber tree plantation, plots with the tropical weed Axonopus compressus were grown under natural outdoor conditions (plot dimensions 2×5 m). The herbicides or their mixtures in a tank mix were applied under standard conditions using a plot spayer at a water application rate of 450 liters of water per hectare (over-the-top application). At intervals of 4, 7, 13, 17 and 21 weeks after the application, the herbicidal efficacy of the active compounds or active compound mixtures was evaluated visually on the basis of the treated plots, in comparison with untreated control plots. The damage to and development of all above-ground parts of the plants were recorded. Evaluation was carried out as described in Example 1. The results are summarized in Table 3.

The comparison of the evaluation values shows that the three-component mixture (trial 1) has considerably better long-term activity than the sum of the herbicidal activities of the individual herbicides (see the experiments after 13 to 21 weeks after application).

TABLE 3

Herbicidal activity against *Axonopus compressus* in rubber tree plantation

| No. | Active compound(s) | Dose (g of AS/ha) | Activity (%), w. after appl. | | | | |
|---|---|---|---|---|---|---|---|
| | | | 4 | 7 | 13 | 17 | 21 |
| 1 | A1.2 + B1 + C1 | 60 + 50 + 40 | 70 | 80 | 80 | 80 | 70 |
| 2 | A1.2 | 60 | 17 | 10 | 0 | 0 | 0 |
| 3 | B1 | 50 | 35 | 35 | 45 | 45 | 50 |
| 16 | C1 | 40 | 5 | 5 | 0 | 0 | 0 |

Abbreviations for Table 3:See abbreviations for Table 1

Example 4

Field Trial

In a sugar cane plantation, plots with the weeds Brachiaria mutica, Digitaria horizontalis, Panicum maximum, Echinochloa colona and Ageratum conyzoides were grown under natural outdoor conditions (dimensions of the plots 2×5 m). The herbicides or their mixtures in a tank mix were applied under standard conditions (over-the-top application using a plot sprayer, water application rate 450 l/ha). Four weeks after the application, the herbicidal efficacy of the active compounds or their mixtures was evaluated visually on the basis of the treated plots, in comparison with untreated control plots. The damage to and development of all above-ground parts of the plants were recorded. Evaluation was carried out as described in Example 1. The results are summarized in Table 4.

The comparison of the evaluation values shows that the three-component mixture (trial 1) has a considerably better average activity and broader activity spectrum than the activity of component A1.2 at a higher application rate.

TABLE 4

Herbicidal activity against weeds in sugar cane plantation

| No. | Active compound(s) | Dose (g of AS/ha) | [1]Herbicidal activity (%) | [2]Weed coverage (%) |
|---|---|---|---|---|
| 1 | A1.2 + B1 + C1 | 100 + 100 + 80 | 92 | 4 |
| 2 | A1.2 | 300 | 72 | 27 |

Abbreviations for Table 4:
[1]Average herbicidal activity in percent, four weeks after application; average value for the five weeds *Brachiaria mutica, Digitaria horizontalis, Panicum maximum, Echinochloa colona* and *Ageratum conyzoides*
[2]Weed coverage in percent ground coverage; control plot has more than 95% weed coverage.

What is claimed is:
1. A herbicidal composition, which comprises an effective amount of a combination of
  A) one or more leaf-acting herbicides from the group of the compounds of the formulae (A1) and (A2) and their esters and salts,

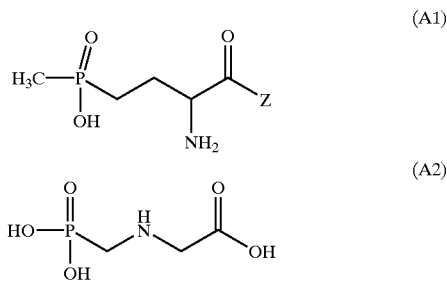

in which Z is a radical of the formula —OH or a peptide radical of the formula —NHCH(CH$_3$)CONHCH(CH$_3$)COOH or —NHCH(CH$_3$)CONHCH[CH$_2$CH(CH$_3$)$_2$]COOH,
  B) one or more active compounds from the group of the imidazolinone herbicides and their salts,
  C) one or more active compounds from the group of the growth-promoting herbicides and their esters and salts.
2. The herbicidal composition as claimed in claim 1, which comprises, as herbicide (A), a herbicide from the group D,L-glufosinate, D,L-glufosinate-ammonium, L-glufosinate, L-glufosinate-ammonium, bialaphos and bialaphos-sodium, glyphosate, glyphosate-sodium, glyphosate-monoisopropylammonium, sulfosate and glyphosate-monoethyl ester and their mixtures.
3. The herbicidal composition as claimed in claim 1, which comprises, as herbicide (B), a herbicide from the group imazapyr, imazethapyr, imazamethabenz, imazamethabenz-methyl, imazamox, imazaquin, AC 263, 222 and salts and esters of the abovementioned herbicides and mixtures of the abovementioned herbicides.
4. The herbicidal composition as claimed in claim 1, which comprises, as herbicide (C), a herbicide from the group 2,4-D, MCPA, 2,3,6-TBA, mecoprop, mecoprop-P, dichlorprop, dichlorprop-P, 2,4-DB, MCPB and dicamba and their salts, esters and mixtures of the abovementioned herbicides.
5. The herbicidal composition as claimed in claim 1, which comprises, as herbicides, a combination of (A) glufosinate-ammonium, (B) imazapyr and (C) 2,4-D-sodium salt.
6. The herbicidal composition as claimed in claim 1, wherein the weight ratios A:B:C of the combined herbicides A, B and C are in the range from 1:0.5:0.5 to 1:2:2.

7. The herbicidal composition as claimed in claim 1, which comprises 1–99% by weight of herbicides and 99–1% by weight of formulation agents which are customary in crop protection.

8. A method for controlling undesirable vegetation, which comprises applying one or more herbicides (A) with one or more herbicides (B) and one or more herbicides (C) onto the harmful plants, plant parts thereof or the area under cultivation, where the combination of the herbicides (A), (B) and (C) is as defined in claim 1.

* * * * *